United States Patent
Hiles

(10) Patent No.: US 10,235,859 B1
(45) Date of Patent: Mar. 19, 2019

(54) SYSTEMS AND METHODS FOR THE MITIGATION OF DROWSY OR SLEEPY DRIVING

(71) Applicant: STATE FARM MUTUAL AUTOMOBILE INSURANCE COMPANY, Bloomington, IL (US)

(72) Inventor: Brian Todd Hiles, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

(21) Appl. No.: 15/679,922

(22) Filed: Aug. 17, 2017

(51) Int. Cl.
| | |
|---|---|
| G08B 23/00 | (2006.01) |
| G08B 21/06 | (2006.01) |
| B60K 28/06 | (2006.01) |
| A61B 5/18 | (2006.01) |
| B60W 40/09 | (2012.01) |
| B60W 40/08 | (2012.01) |

(52) U.S. Cl.
CPC ............... G08B 21/06 (2013.01); A61B 5/18 (2013.01); B60K 28/066 (2013.01); B60W 40/09 (2013.01); B60W 2040/0827 (2013.01)

(58) Field of Classification Search
CPC .. G08B 21/06; B60K 28/066; H04N 5/23229; A61B 5/18; A61B 5/746
USPC .................................................. 340/575, 576
See application file for complete search history.

(56) References Cited

U.S. PATENT DOCUMENTS

| | | | | | |
|---|---|---|---|---|---|
| 5,907,282 | A | * | 5/1999 | Tuorto ................... | G08B 21/06 340/439 |
| 9,682,622 | B2 | * | 6/2017 | Kim ..................... | H04N 5/23229 |
| 9,809,228 | B2 | * | 11/2017 | Hong ..................... | B60W 40/08 |
| 2015/0025917 | A1 | * | 1/2015 | Stempora ............... | G06Q 40/08 705/4 |
| 2015/0351681 | A1 | * | 12/2015 | Lee ....................... | A61B 5/4806 600/595 |

OTHER PUBLICATIONS

Facts and Stats: Drowsy Driving—Stay Alert, Arrive Alive, National Sleep Foundation, 2017, http://drowsydriving.org/about/facts-and-stats/, 3 pages.

\* cited by examiner

*Primary Examiner* — Toan N Pham
(74) *Attorney, Agent, or Firm* — Marshall, Gerstein & Borun LLP; Randall G. Rueth

(57) ABSTRACT

Systems and methods for mitigating drowsy and/or sleepy driving may include utilizing vehicle-related and wellness-related telematics to detect and/or predict drowsy and/or sleepy driving states of a driver of a vehicle and take mitigating actions to thereby increase the safety of the driver and other people and/or vehicles in the vicinity of the driver's vehicle. Vehicle-related telematics data and wellness-related telematics data (which may include sleep data) may be collected via sensors that disposed on-board the vehicle, in the vehicle's environment, and at a personal health/fitness tracker of the driver. The collected data may be collectively interpreted to detect, predict, and/or otherwise discover information relating to a drowsy and/or sleepy state of the driver, and one or more mitigating actions may be automatically performed based on the discovered information to thereby mitigate undesirable effects of drowsy/sleepy driving and increase driving safety.

21 Claims, 5 Drawing Sheets

SYSTEMS AND METHODS FOR THE MITIGATION OF DROWSY OR SLEEPY DRIVING

FIELD OF THE DISCLOSURE

The present disclosure generally relates to mitigating drowsy and/or sleepy driving and improving driving safety based on vehicle-related and sleep-related telematics data.

BACKGROUND

Driving vehicles while drowsy and falling asleep at the wheel are dangerous behaviors that cause car accidents, injuries, deaths, and monetary losses. Driving while drowsy or sleepy often garners comparisons to driving while chemically impaired (e.g., by alcohol) due to its disastrous consequences. However, while breathalyzer and blood tests are available to test for alcohol-impaired driving, tests to detect or determine whether a driver is driving while drowsy or sleepy are not readily available. Furthermore, self-reporting of drowsy and/or sleepy driving tends to be unreliable. As a result, drivers are not currently well-informed of the degree to which they are drowsy or sleepy, nor are drivers knowledgeable regarding their drowsy and/or sleepy driving habits, thus increasing the risk to them and others when they operate vehicles while drowsy or falling asleep.

SUMMARY

The present disclosure generally relates to systems, methods, devices, apparatuses, and techniques for mitigating drowsy or sleepy driving and improving driving safety based on vehicle-related and sleep-related telematics data. Embodiments of example systems, methods, devices, apparatuses, and techniques are summarized below. The example systems, methods, devices, apparatuses, and techniques summarized below may include additional, less, or alternate actions, and/or additional, less, or alternate components, including those discussed elsewhere herein.

In an embodiment, a system for mitigating drowsy and/or sleepy driving may include a set of sensors disposed on-board a vehicle operated by a driver; a personal tracking device that senses one or more physiological conditions of the driver; and one or more computing devices that are communicatively connected to the set of of on-board sensors of the vehicle and to the personal tracking device. The one or more computing devices may include one or more processors, one or more memories, and a set of computer-executable instructions stored on the one or more memories and executable by the one or more processors to: collect, via one or more communication channels, vehicle-related telematics data generated by the set of on-board sensors of the vehicle; collect, via the one or more communication channels, wellness-related telematics data generated by the personal tracking device based on the sensed physiological conditions of the driver, the wellness-related telematics data including sleep data indicative of at least one of a quality or a duration of sleep achieved by the driver; interpret the vehicle-related telematics data in conjunction with the wellness-related telematics data, thereby generating information indicative of a drowsy and/or sleepy state of the driver; and cause a mitigating action to be performed based on the generated information indicative of the drowsy and/or sleepy state of the driver.

In an embodiment, a method for mitigating drowsy and/or sleepy driving may include collecting, via one or more communication channels by one or more computing devices, vehicle-related telematics data generated by a set of sensors monitoring at least one of a condition or a behavior of a vehicle operated by a driver; collecting, via the one or more communication channels by the one or more computing devices, wellness-related telematics data generated by a personal tracking device that senses physiological conditions of the driver, the wellness-related telematics data based on the sensed physiological conditions of the driver, and the wellness-related telematics data including sleep data that is indicative of at least one of a quality or a duration of sleep achieved by the driver; interpreting, at the one or more computing devices, the vehicle-related telematics data in conjunction with the wellness-related telematics data, thereby generating information indicative of a drowsy and/ or sleepy state of the driver; and transmitting, by the one or computing devices, a command for a mitigating action to be performed, the command for the mitigation action based on the generated information indicative of the drowsy and/or sleepy state of the driver.

In an embodiment, a tangible, non-transitory computer-readable medium may store instructions for mitigating drowsy and/or sleepy driving. The stored instructions, when executed by one or more processors of a computer system, may cause the computer system to: collect, via one or more communication channels, vehicle-related telematics data generated by a set of sensors monitoring at least one of a condition or a behavior of a vehicle operated by a driver; collect, via the one or more communication channels, wellness-related telematics data generated by a personal tracking device that senses physiological conditions of the driver, the wellness-related telematics data based on the sensed physiological conditions of the driver, and the wellness-related telematics data including sleep data that is indicative of at least one of a quality or a duration of sleep achieved by the driver; interpret the vehicle-related telematics data in conjunction with the wellness-related telematics data, thereby generating information indicative of a drowsy and/or sleepy state of the driver; and transmit a command for a mitigating action to be performed, the command for the mitigation action based on the generated information indicative of the drowsy and/or sleepy state of the driver.

Systems or computer-readable media storing executable instructions for implementing all or part of the systems, techniques, apparatuses, devices, and/or methods described herein may also be provided in some embodiments. Systems and/or components for implementing all or parts of the systems, techniques, apparatuses, devices and/or methods described herein may include one or more of the following: a special-purpose computing device, a mobile computing device, a personal electronic device, an on-board computer, one or more remote servers or cloud computing systems, one or more remote data storage entities, devices, or systems, one or more sensors, one or more communication modules configured to communicate wirelessly via radio links, radio frequency links, and/or wireless communication channels, and/or one or more non-transitory, tangible program memories coupled to one or more processors of the special-purpose computing device, mobile computing device, personal electronic device, on-board computer, and/or one or more remote servers or cloud computing systems. Such program memories may store instructions, which, when executed by one or more processors, may cause a system, device, and/or apparatus described herein to implement part or all of one or more methods described herein. Additional or alternative features described herein below may be included in some embodiments.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary arrangements, except as may be explicitly delineated in the corresponding written description. None of the drawings are necessarily to scale.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

Figure 1:
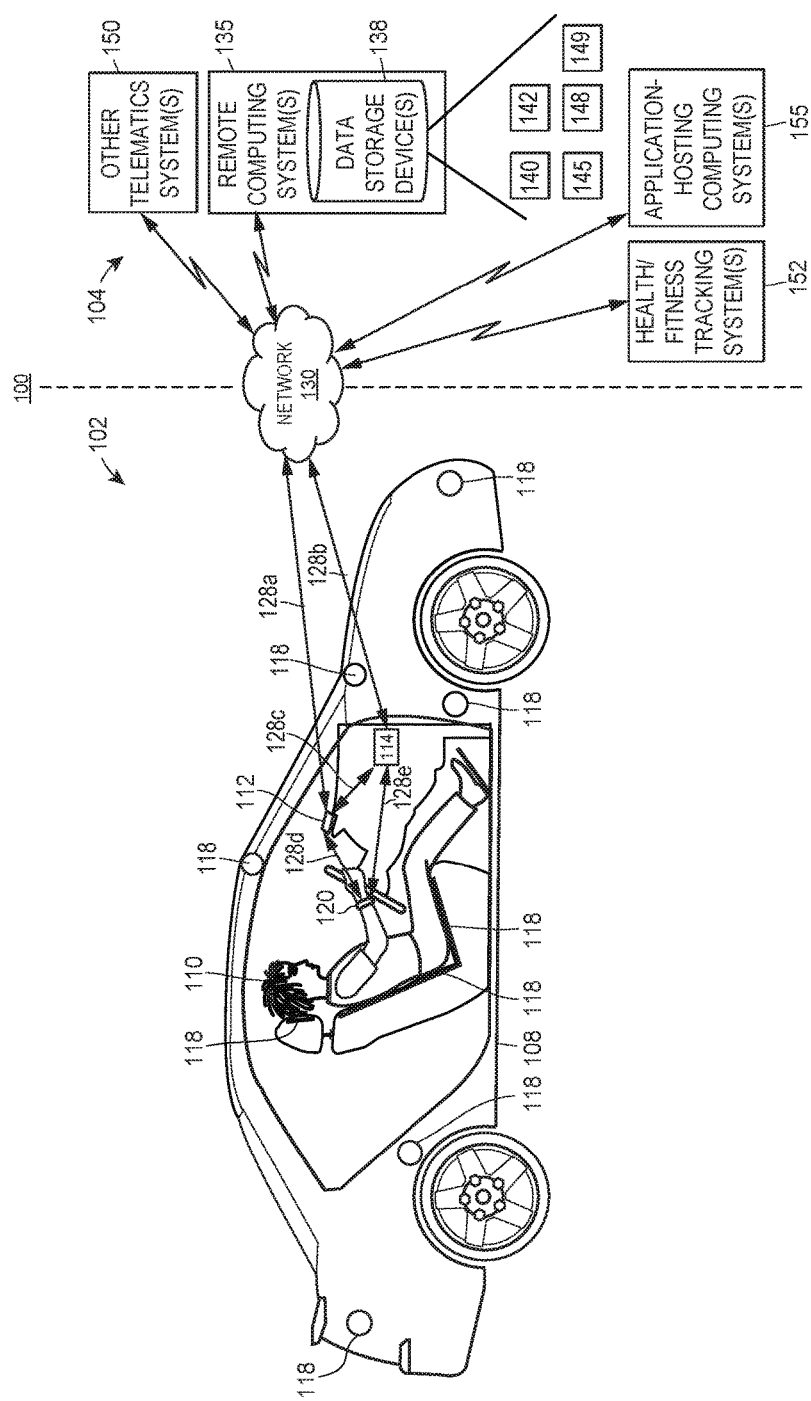

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Thus, the figures depict preferred embodiments for purposes of illustration only. Alternative arrangements of the systems and methods illustrated herein may be employed without departing from the principles of the invention described herein. Furthermore, wherever possible, the following description refers to the reference numerals included in the following figures, in which features depicted in multiple figures are designated with consistent reference numerals.

Figure 2:
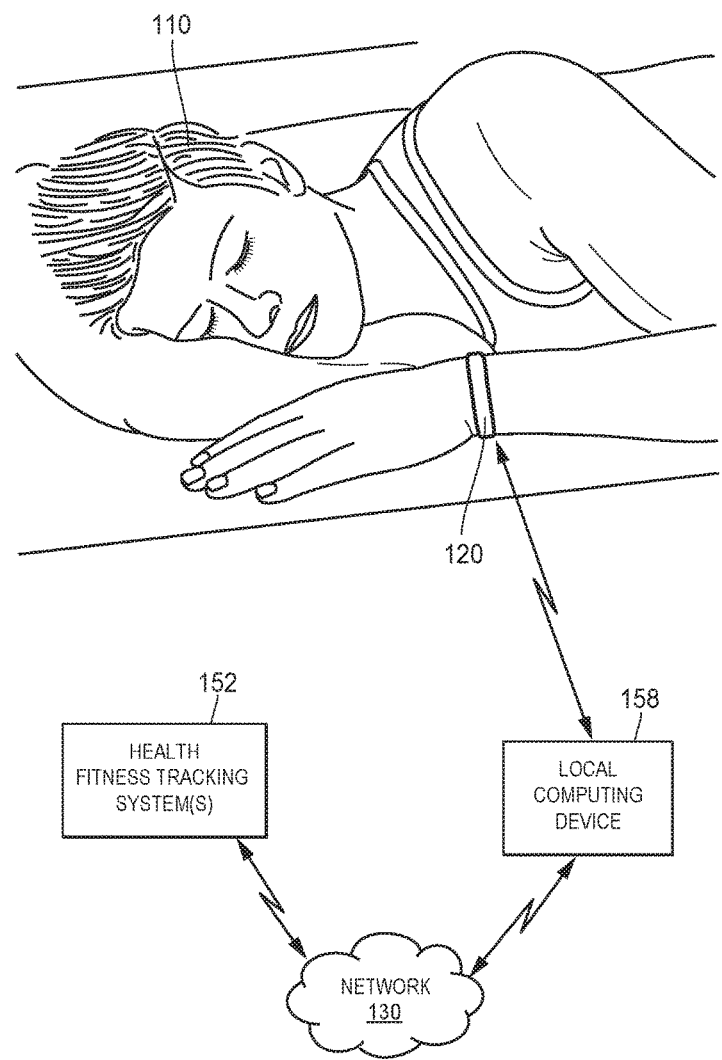
Figure 3:
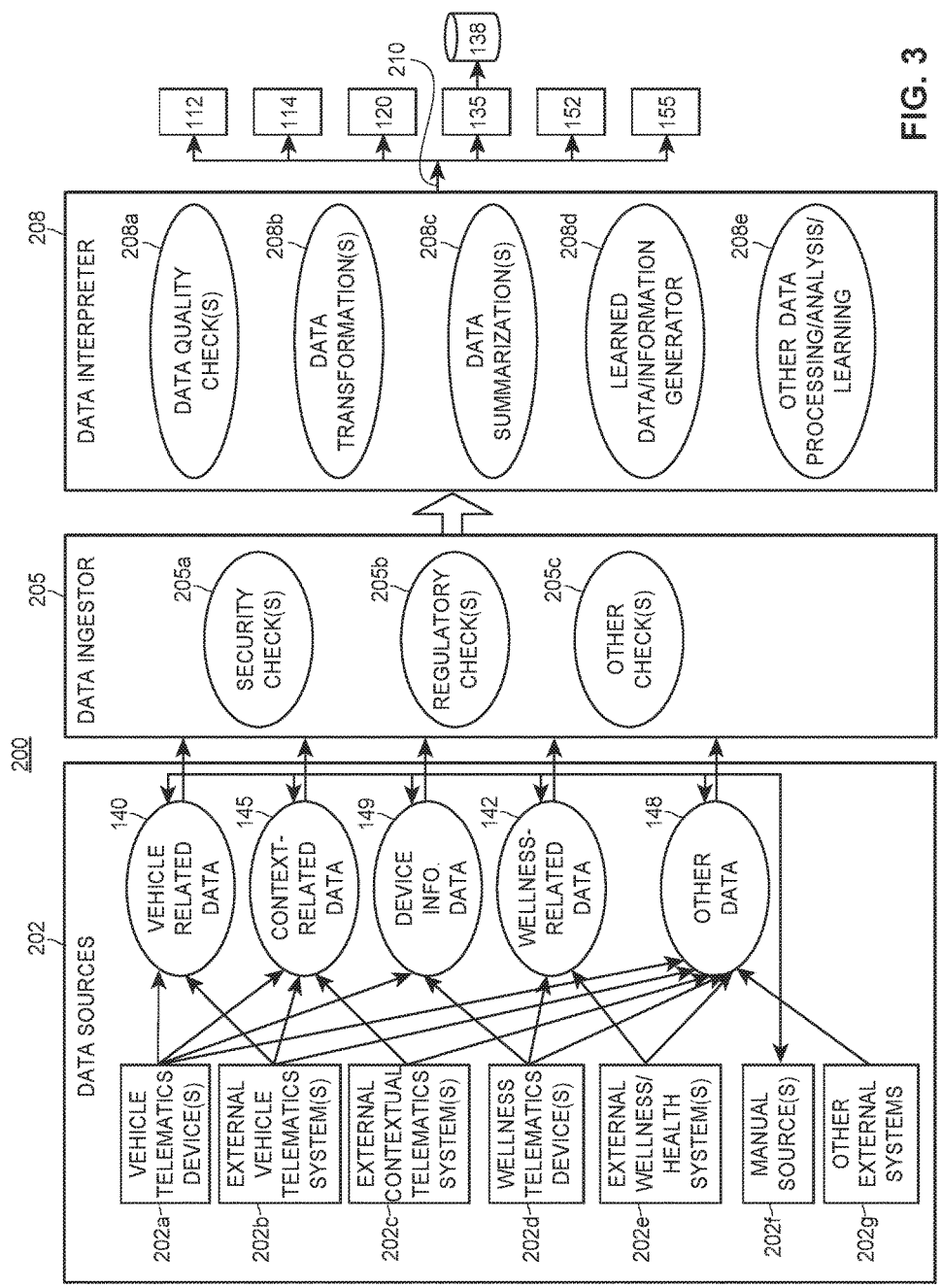
Figure 4:
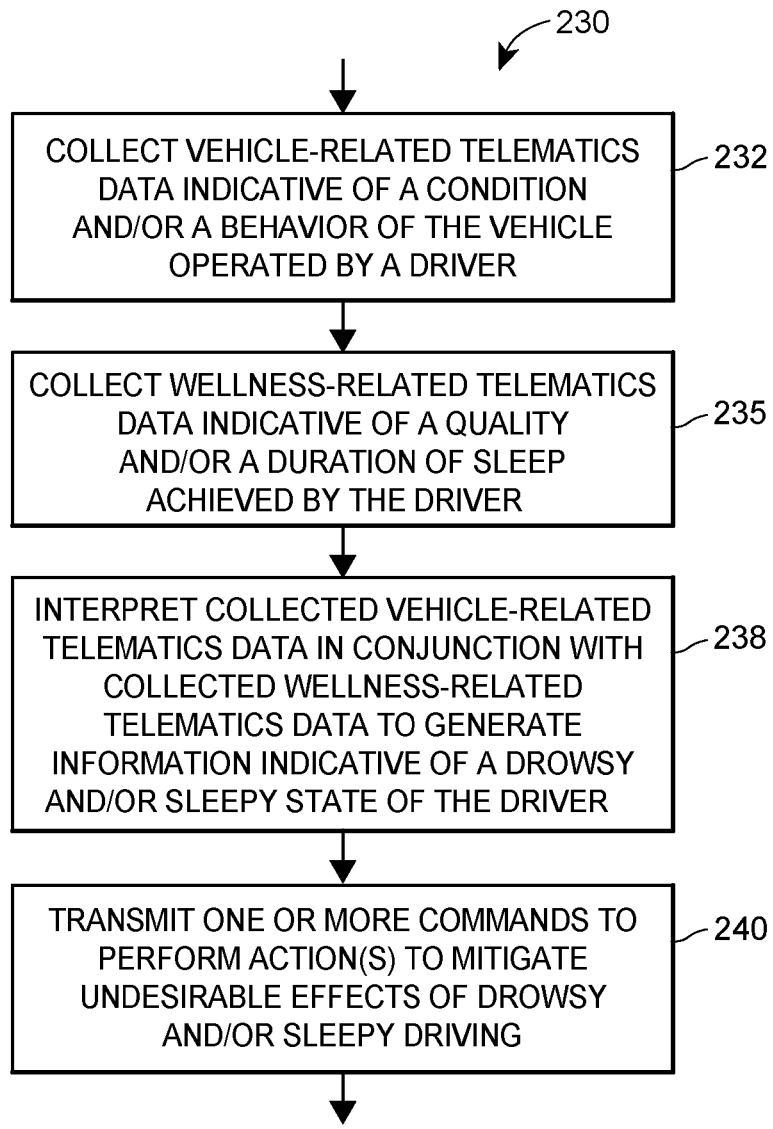
Figure 5:
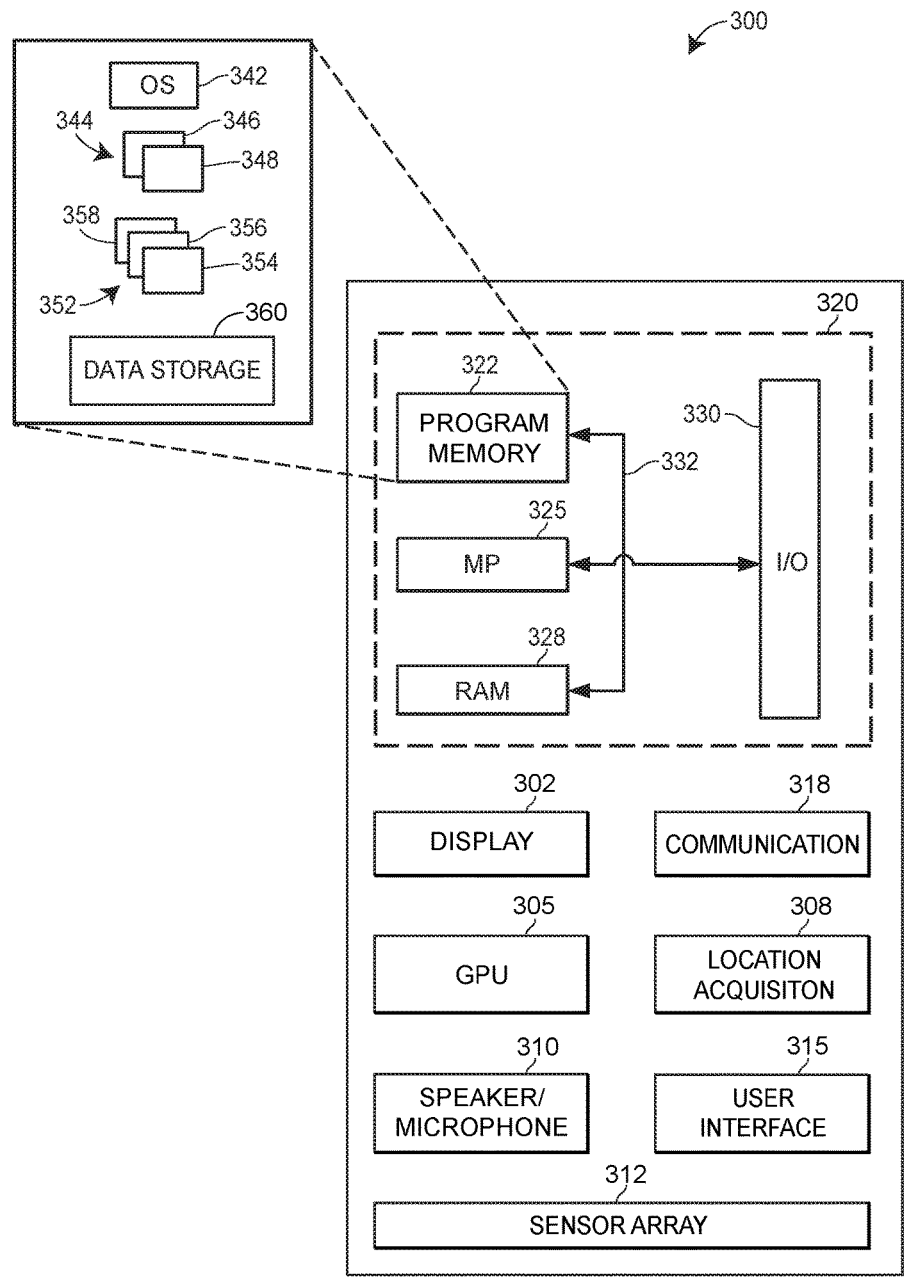

FIG. 1 illustrates an exemplary vehicle-related data collection system of a vehicle in accordance with an exemplary aspect of the present disclosure;

FIG. 2 illustrates an exemplary personal health or fitness tracking device which may be worn by a user in accordance with an exemplary aspect of the present disclosure;

FIG. 3 illustrates a block diagram of an exemplary data flow diagram which may occur in embodiments of systems, methods, and/or techniques for mitigating drowsy or sleepy driving disclosed herein;

FIG. 4 depicts an flow diagram of an example method for mitigating drowsy or sleepy driving; and FIG. 5 illustrates a block diagram of an exemplary computing device in accordance with aspects of embodiments of the systems, methods, and/or techniques for mitigating drowsy or sleepy driving disclosed herein.

DETAILED DESCRIPTION

Generally speaking, the novel systems, methods, devices, apparatuses, and/or techniques discussed in the present disclosure relate to collecting, transmitting, and/or receiving vehicle-related telematics data and sleep-related telematics data, and using or interpreting the collected data to determine, detect, and/or predict the driving safety level of a vehicle driver with respect to drowsy and/or sleepy driving, and cause one or more mitigating actions to be performed to thereby increase the safety of the driver as well as to other vehicles and people in the vicinity of the driver's vehicle. The novel systems, methods, devices, apparatuses, and/or techniques discussed in the present disclosure may also relate to other useful applications related to mitigating drowsy and/or sleeping driving and increasing driving safety. Accordingly, the novel systems, methods, devices, apparatuses, and techniques disclose herein may include specifically configured computing equipment that provide for an enhanced method of collecting vehicle-related telematics data and sleep-related telematics data and performing certain actions based upon the collected data. For example, a mobile device, a personal health device such as an activity tracker or CPAP machine, a vehicle-mounted processor, a remote computer server or cloud computing system, web pages, applications, software modules, user interfaces, interactive display screens, memory units, and/or other electronic, electrical, and/or wireless communication equipment may be specifically configured to provide at least some of the functionality discussed herein.

FIG. 1 illustrates a block diagram of an exemplary system 100 for mitigating drowsy or sleepy driving in accordance with an exemplary embodiment of the present disclosure. The system 100 may include hardware and software applications and/or modules, as well as various data communications channels for communicating data between the various hardware and software components, as is described below. The system 100 may be roughly divided into front-end components 102 and back-end components 104. The front-end components 102 may be particularly positioned and/or configured to detect, measure, calculate, generate, and/or collect driving-related and/or vehicle-related data indicative of the speed, direction, motion, and/or behavior of a vehicle 108. Additionally or alternatively, the front-end components 102 may include hardware and software applications and/or modules that are particularly positioned and/or configured to detect, receive, and/or process data indicative of times during which the vehicle 108 is being driven by a user 110, an amount of pedestrian traffic experienced by the vehicle 108 during use, the type of streets that the vehicle 108 travels through during use, other conditions occurring in the environments in which the vehicle 108 is operating, driving violations that are/were committed while the driver 110 is operating the vehicle 108, and/or other vehicle-related data. For example, as shown in FIG. 1, the system 100 may include one or more mobile computing devices 112, one or more on-board computing devices 114 that are fixedly connected to the vehicle 108, and a set of sensors 118 that are disposed at various locations on-board the vehicle 108, e.g., "on-board sensors 118." As further shown in FIG. 1, the system 100 for mitigating drowsy or sleepy driving may include a personal health or fitness tracking device 120 associated with the driver 110, which typically (but not necessarily) may be worn or otherwise ported by the driver 110. Further, the system 100 may include various wired and/or wireless data communication channels (e.g., as denoted by references 128a-128e) for facilitating data communications between the various hardware and software components and/or communications disposed within the vehicle 108, such as those included in the computing devices 110, 114, the on-board sensors 118, the personal tracking device 120, and, in some embodiments, with one or more back-end components 104 of the system 100.

In some embodiments (not shown in FIG. 1), the personal health or fitness tracking device 120 and the mobile computing device 112 may be an integral device. However, for clarity of discussion and not for limitation purposes, the personal tracking device 120 and the mobile computing device 112 are referred to herein as separate and distinct devices. In some embodiments (also not shown in FIG. 1), the mobile computing device 112 and the on-board computing device 114 may be an integral device; however, for clarity of discussion and not for limitation purposes, the mobile computing device 112 and the on-board computing device 114 are referred to herein as separate and distinct devices. Further, in some embodiments (also not shown in FIG. 1), the mobile computing device 112 and the personal tracking device 120 may be an integral device; however, for clarity of discussion and not for limitation purposes, the mobile computing device 112 and the personal tracking device 120 are referred to herein as separate and distinct devices. At any rate, the mobile computing device 112 and the on-board computing device 114 may share any suitable portion of processing between one another to facilitate any of the functionality described herein, or may not share any processing at all between one another to facilitate any of the functionality described herein. Further, in some embodiments, the vehicle 108 may include multiple mobile computing devices 112 and/or multiple on-board computing devices 114; however, again for clarity of discussion and not for limitation purposes, the mobile computing device 112 and the on-board computing device 114 are referred to herein using the singular tense. Each of the computing devices 110, 114 included in the system 100 may be disposed within the vehicle 108, permanently installed in the vehicle 108, or removably installed in the vehicle 108, as desired. In some embodiments, the mobile computing device 112 is omitted from the vehicle 108, and in some embodiments, the on-board computing device 114 is omitted from the vehicle 108.

In some embodiments, the mobile computing device 112 may be associated with (e.g., owned, operated by, and/or carried or ported by) the driver 110, and may be implemented as any suitable personal electronic device (PED), such as a mobile electronic device (e.g., smartphone, tablet, laptop, wearable electronics, phablet, pager, personal digital assistant (PDA), smart glasses, smart watch or bracelet, etc.). The on-board computing device 114 may implemented as an on-board computer or processor(s) that are installed by the manufacturer of the vehicle 108 or that is added to the vehicle 108 as an aftermarket modification to the vehicle 108, for example. In some embodiments, the mobile computing device 112 and/or on-board computing device 114 may be thin-client devices configured to outsource any suitable portion of processing via communications with one or more back-end components 104, e.g., via the links 128a, 128b, and one or more networks 130. In some embodiments, the on-board computing device 114 may supplement one or more functions performed by mobile computing device 112 described herein (and/or vice versa) by, for example, sending information to and/or receiving information from mobile computing device 112 via the wireless link 128c.

In one embodiment, the mobile computing device 112 may be configured with suitable hardware and/or software (e.g., one or more applications, programs, files, etc.) to determine a geographic location of mobile computing device 112 and, hence, the vehicle 108 when the mobile computing device 112 is disposed in the vehicle 108. Additionally or alternatively, the mobile computing device 112 may be configured with suitable hardware and/or software to monitor, measure, generate, and/or collect one or more sensor metrics (e.g., data generated by the sensors of the mobile computing device 112) as part of the driving data. That is, the mobile computing device 112 may integrally include one or more of the on-board sensors 118. In some scenarios, the mobile computing device 112 may be configured to transmit or provide the geographic location data and/or the one or more sensor metrics or data to the on-board computing device 114 and/or to one or more external components, such as one or more back-end components 104.

The on-board computing device 114 may be configured to perform one or more functions otherwise performed by mobile computing device 112. However, on-board computing device 114 may additionally or alternatively be configured to obtain driving- or vehicle-related data by communicating with one or more on-board sensors 118 that are integrated into or disposed within the vehicle 108. For example, on-board computing device 114 may obtain geographic location data via communication with a vehicle-integrated global navigation satellite system (GNSS). To provide additional examples, on-board computing device 114 may obtain one or more metrics or data related to the speed, direction, and/or motion of vehicle 108 via any number of suitable on-board sensors 118, such as speedometer sensors, braking sensors, airbag deployment sensors, crash detection sensors, accelerometers, etc.

In some embodiments of the system 100, the front-end components 102 may communicate collected sensor data to the back-end components 104, e.g., via the one or more networks 130. For example, at least one of the on-board computer 114 or the mobile device 112 may communicate with the back-end components 104 via the network(s) 130 to allow the back-end components 104 to record or store collected sensor data and information regarding vehicle usage, vehicle operations, vehicle telematics data, and/or other vehicle-related data. The network(s) 130 may include a proprietary network, a secure public internet, a virtual private network, and/or some other type of network, such as dedicated access lines, plain ordinary telephone lines, satellite links, packet data networks, wired data networks, wireless data networks, wired communications networks, wireless communication networks, combinations of these and/or other types of networks. The network(s) 130 may utilize one or more radio frequency communication links to communicatively connect to the vehicle 108, e.g., may utilize wireless communication links 128a and 128b to communicatively connect with the mobile device 112 and the on-board computer 114, respectively. Where the network(s) 130 comprise the Internet or other data packet network, data communications may take place over the network 130 via an Internet or other suitable data packet communication protocol. In some arrangements, the network(s) 130 additionally or alternatively includes one or more wired communication links or networks. Although in certain embodiments the network(s) 130 may include multiple networks, the network 130 is referred to herein using the singular tense for clarity of discussion, and not for limitation purposes.

The back-end components 104 may include one or more servers or computing devices 135, which may be implemented as a network server, a web-server, a database server, a bank of servers, a computing cloud, and/or any suitable combination thereof, and is interchangeably referred to herein as a "remote computing system 135." The remote computing system 135 may include one or more computer processors adapted and configured to execute various software applications and components of the system 100, in addition to other software applications. The remote computing system 135 may further include or be communicatively connected to one or more data storage devices or entities 138, which may be adapted to store various types of data 140, 142, 145, 148. For example, the data storage devices or entities 138 may store data related to the vehicle 108 and/or operation of the vehicle 108 by its driver 110 (e.g., "vehicle-related data 140"), such as vehicle telematics data, vehicle behavior data, vehicle operations data, data indicative of driver-initiated actions occurring during the driver's operation of the vehicle 108, sensed or obtained information indicative of environmental conditions while the driver 110 is operating the vehicle 108, etc. The data storage devices or entities 138 may store data 142 related to wellness and/or health of the driver 110 (e.g., "wellness-related data 142"), such as various types of sleep-related data and/or other types of wellness data indicative of various physiological characteristics, conditions, and/or behaviors of the driver 110. In some embodiments, the data storage devices or entities 138 may store data 145 related to contexts and/or environments in which the vehicle 108 is operating and/or has operated (e.g., "context-related data 145"). Examples of context-related data 145 may include weather conditions, road conditions, road quality, levels of congestion, pedestrian density, construction, route topology, etc. Of course, the data storage entities 138 may store other types of data 148 which may be related to mitigating drowsy or sleepy driving, for example, historical driving data of the driver (e.g., historical telematics data, insurance claims, how long the driver has been on the road, etc.), shift work or other job related records, and/or any other types of data which may be related to mitigating drowsy or sleepy driving.

The one or more data storage devices 138 may be implemented using any suitable tangible, non-transitory computer readable storage media and/or memories, at least a portion of which may be included in the remote computing system 135 (as depicted in FIG. 1), and/or at least a portion of which may be excluded from the remote computing system 135 but nonetheless accessible to the remote computing system 135 (not shown in FIG. 1). For example, the one or more data storage devices 138 may be implemented as a data bank or a cloud data storage system, at least a portion of which may be locally accessed by the remote computing system 135 using a local access mechanism such as a function call or database access mechanism, and/or at least a portion of which may be remotely accessed by the remote computing system 135 using a remote access mechanism such as a communication protocol. At any rate, the remote computing system 135 may access the data 140, 142, 145, 148 stored in the one or more data storage devices 138 when executing various functions and tasks associated with the present disclosure. In some embodiments, the mobile computing device 112 and/or the on-board computing device 114 may access the data 140, 142, 145, 148 stored in the remote data storage devices 138 when executing various functions and tasks associated with the present disclosure, for example, via the network 130, and optionally the remote computing system 135.

In some embodiments, at least a portion of the vehicle-related data 140 and/or the context-related data 145 may be transmitted from or provided by one or more other (e.g., remote) telematics collection systems 150, e.g., via the network 130, and optionally via the remote computing system 135. The one or more other telematics collection systems 150 may include, for example, infrastructure sensing systems such as systems that are used to support autonomous vehicles, city or jurisdictional sensor systems, Internet-of-Things (IOT) systems, weather data systems, etc. In some situations, the other telematics collection systems 150 may include one or more other vehicles that are in communicative connection with the mobile computing device 112, with the on-board computing device 114, and/or with the remote computing system 135. In some embodiments, each telematics collection system 150 may transmit or provide respective data, data file(s), and/or a data feed or data stream of content. At least some of the telematics collection systems 150 may be owned and/or operated by a respective telematics vendor or provider, for example.

Moreover, in the system 100, the mobile computing device 112, the on-board computing device 114, and/or the remote computing system 135 may operate (either independently or at least partially in conjunction) to receive wellness-related data 142 associated with the driver 110. The wellness-related data 142 of the driver 110 may be generated based user conditions, characteristics, and/or conditions that are sensed by the personal health or fitness tracking device 120. The wellness-related data 142 of the driver 110 may be provided at least partially directly by the personal tracking device 120, and/or may be provided at least partially by a health or fitness tracking system 152 (e.g., a remote health or fitness tracking system 152) with which the personal tracking device 120 uploads and/or synchronizes its data. For example, the mobile computing device 112, the on-board computing device 114, and/or the remote computing system 135 may receive at least a portion of the wellness-related data 142 associated with the user 110 via one or more wired and/or wireless communications channels 128d, 128e within the vehicle 108 while the personal tracking device 120 is being transported by the vehicle 108. Additionally or alternatively, the mobile computing device 112, the on-board computing device 114, and/or the remote computing system 135 may receive at least some of the wellness-related data 142 of the user 110 from the fitness tracking system 152, e.g., via the network 130. The health/fitness tracking system 152 may be implemented in any suitable manner, such as by one or more servers or by a computing cloud. Received wellness-related data 142 may be stored in the data storage devices 138, in an embodiment.

As previously discussed, wellness-related data 142 of the user 110 may include, inter alia, sleep data. The term "sleep data," as used herein, generally refers to data that is sensed, collected, and/or generated by the personal health or fitness tracking device 120 and that may be associated with the sleep quality and/or duration of user 110 at various instances in and over time. The sleep data of the user 110 may include data generated or obtained from one sleep cycle and/or time period (which may include times of both wakefulness and sleep), or may include data generated or obtained across multiple sleep cycles and/or multiple time periods (which may include times of both wakefulness and sleep). As such, the term "sleep data," as used herein, may refer to aggregate sleep data (e.g., averages, cumulative, quality of sleep over time, etc.) in addition or alternatively to sleep data pertaining to a single sleep cycle. For example, sleep data may include a total number of hours of uninterrupted sleep achieved by the user 110 during a period of time, a number of REM (Rapid-Eye-Movement) cycles achieved by the user 110 during a period of time, an number of restless sleep periods, durations of wakefulness prior to a sleep cycle, etc. In some implementations, sleep data may include one or more results of comparing achieved sleep data against target sleep data. For example, sleep data may include a sleep shortage value based on a comparison of achieved sleep data and target sleep data, where the sleep shortage value is indicative of the number of times that the total number of hours of uninterrupted sleep is less than the target number of hours of uninterrupted sleep within a set period of time. In another example, sleep data may include a REM shortage value indicative of a REM cycles shortage number equal to the number of times that the number of REM cycles achieved is less than the target number of REM cycles within the set period of time. Of course, other types of sleep data, both sensed and derived, may be possible.

At least some portion of sleep data of the user 110 may be obtained by the mobile computing device 112 and/or the on-board computer 114 directly from the personal health or fitness tracking device 120, e.g., via the wireless links 128*d*, 128*e*. Additionally or alternatively, at least some portion of sleep data of the user 110 may be obtained by the mobile computing device 112 and/or by the on-board computer 114 from one or more back-end components 104, e.g., via the wireless links 128*a* 128*b*. For example, the mobile computing device 112 and/or the onboard computer 114 may obtain the user sleep data from the fitness tracking system 152 with which the user 110 synchronizes his or her personal tracking device 124 or to which the user 110 uploads data from the personal tracking device 120. For instance, the mobile computing device 112 and/or the on-board computing device 114 may obtain at least some wellness-related data 142, including sleep data, from the fitness tracking system 152 via the network 130 and the wireless links 128*a*, 128*b*, and/or from the fitness tracking system 152 via the remote computing system 135, the network 130, and the wireless links 128*a*, 128*b*. Generally speaking, a user's sleep data may include indications of a date, time, and/or time period during which sleep data points were collected or sensed, and any aggregation, comparisons, summarizations, calculations, and/or analyses thereof. In a similar manner, other wellness-related data 142 (e.g., heart rate, blood pressure, calories ingested, oxygen concentration, blood sugar levels, and/or other physiological data, which may be collected over time) of the user 110 may be obtained and stored.

FIG. 2 illustrates a personal health or fitness tracking device 120 which may be worn by the user 110 while sleeping, in accordance with an exemplary aspect of the present disclosure. The personal health or fitness tracking device 120 may be or include, among other options, an activity tracker, a heart rate monitor, headphones, a thermometer, a CPAP (Continuous Positive Airway Pressure) machine, a BiPAP (Bilevel Positive Airway Pressure) machine, a smart watch, a flexible electronic patch, fitness clothing, a respiration rate detector, a pulse oximeter, a smart belt, a blood pressure monitor, a hemoglobin tracker, or other type of personal health or fitness device that is configured to sense and collect personal physiological (and optionally, other types of) data associated with its user. The personal tracking device 120 may, in some implementations, not be worn by the user 110 but may track the user's personal data through alternate means such as, among other options, a connected bed or sheets, a medical scanner, a smart mattress, a sonar sleep tracker, a strip or mat sleep tracker, under-mattress compression sensor, and the like. Further, although the embodiments shown and described herein depict a single personal tracking device 120 being included in the system 100 and worn by the user 110, this is for ease of discussion purposes and not limitations. Indeed, in other embodiments, more than one single personal tracking device 120 corresponding to the user may be included in the system 100. For example, wellness-related data 142 of the user 110 may be collected from a personal fitness tracker, a blood pressure monitor, and a CPAP machine.

At any rate, the personal tracking device 120 is configured to sense and collect sleep data indicative of sleep-related and other physiological aspects of the user 110. The sleep data may indicate or include information detailing, for example, elapsed time of uninterrupted sleep, REM cycles experienced by the user, total hours of sleep, number and duration of restless sleep periods, number and duration of intervals of wakefulness, and/or other sleep data. Other information may inform and/or be considered part of the sleep data collected by the personal tracking device 120, such as blood pressure, heart rate, temperature, compression measurements, measurements, pressure measurements, blood sugar measurements, and/or other physiological and other types data of the user 110 that is observed by the personal tracking device 120.

The personal health or fitness tracking device 120 may include one or more data communication channels for facilitating data communications with one or more external components and systems. In an embodiment, the personal tracking device 120 may include one or more wireless transceivers via which collected physiological data is communicated to the one or more external components and systems. For example, data that is collected by the personal tracking device 120 may be provided, via the one or more wireless transceivers, to a local computing device 158 that is owned and/or operated by the user 110, such as a smart phone or device, a tablet, a laptop, or other personal computing device. Subsequently, the data collected by the personal tracking device 120 and/or indications thereof (e.g., aggregate information) may be transferred at least in part from the personal computing device 158, e.g., via the network 130, to the fitness tracking system 152 at which the user's data may be stored. In some arrangements (not shown in FIG. 2), sleep data that is collected by the personal tracking device 120 may be transferred in a wired manner, for example, by using a USB flash drive or other mechanical data transfer mechanism to transfer the collected sleep data from the personal tracking device 120 to the personal computer 158 via which the collected sleep data may be uploaded to the fitness tracking system 152. At any rate, whether transferred wirelessly and/or in a wired manner, the data transfer communications may occur automatically at regular scheduled intervals and/or may be manually scheduled or performed by the user 110.

FIG. 3 illustrates a block diagram of an exemplary data flow diagram 200 which may occur or be implemented in embodiments of systems, methods, and/or techniques for mitigating drowsy or sleepy driving disclosed herein. The data flow 200 may occur or be implemented, for example, at least partially at the mobile computing device 112, at least partially at the on-board computing device 114, and/or at least partially at the remote computing system 135 of FIG. 1. Additionally, data that is obtained, stored, and/or utilized during the data flow 200 may be stored in and/or accessed from one or more tangible, non-transitory memories that are included in or accessible to the mobile computing device 112, the on-board computing device 114, and/or the remote data storage devices 138. For clarity of discussion herein, though, and not for limitation purposes, the data flow 200 is discussed below with simultaneous reference to FIGS. 1 and 2.

As illustrated in the data flow diagram 200, data utilized for mitigating drowsy or sleepy driving may be obtained (e.g., directly and/or indirectly) from one or more data sources 202, e.g., via the network 130 and/or the links 128*a*-128*e*. Various types of data may be obtained from types of data sources 202. For example, one or more vehicle telematics devices 202*a* disposed on-board the vehicle 108 may provide (e.g., be a source of) at least some of the vehicle-related data 140 and/or context-related data 145 associated with the vehicle 108. The on-board vehicle telematics devices 202 may include one or more of the sensors 118 disposed on-board the vehicle 108, and or other devices on-board the vehicle 108. In some embodiments, at least some of the on-board telematics devices 202 may be included in the mobile computing device 112 and/or the on-board computing device 114. On-board vehicle telematics devices 202 may provide data that is indicative of vehicle operations, vehicle behavior, driver behavior and/or actions, quality of vehicle parts, environmental conditions, and/or any other type of data that is sensed at the vehicle 108.

Additionally or alternatively, one or more external vehicle telematics systems 202b may provide or be a source of at least some of the vehicle-related data 140 and/or at least some of the context-related data 145 associated with the vehicle 108. External vehicle telematics systems 202b may include, for example, one or more third-party remote telematics systems 150, which may provide at least some of the vehicle-related data 140 and/or at least some of the context-related data 145 via data files and/or data feeds. In an example, an external vehicle telematics system 202b may receive, store, and/or analyze data that is sensed and provided by one or more on-board vehicle telematics devices 202a, which may be on-board the same or different vehicles. In some embodiments, external vehicle telematics systems 202b may operate in conjunction with (or, in some embodiments, be included integrally with) one or more on-board vehicle telematics systems and/or devices, such as the vehicle telematics devices 202a, the on-board sensors 118, the on-board computing device 114, and/or the mobile computing device 112 of one or more vehicles. External vehicle telematics systems 202b may provide, for example, odometer data, telemetry data (e.g., fine-grained sensor information like GPS coordinates), summarized driving data (e.g., coarse-grained aggregated information like number of turns, etc.), and/or other type of data that is sensed by the systems 202b and that is associated with the vehicle 108 operating in various environments or contexts.

Still additionally or alternatively, one or more external contextual telematics systems 202c may provide at least some of the context-related data 145 associated with the vehicle 108. External contextual telematics systems 202c may include, for example, one or more third-party remote telematics systems 150, and may provide context-related data 145 indicative and/or descriptive of the contexts and/or environments in which the vehicle 108 is or was operating (e.g., weather conditions, road conditions, speed limits, traffic density, pedestrian density, construction zones, etc.)

As also illustrated in FIG. 3, one or more wellness telematics devices 202d may be sources of data that is utilized in the data flow 200. The one or more wellness telematics devices 202d may include, for example, one or more personal health or fitness tracking devices 120 worn or ported by the user 110 and/or any other type of personal health or fitness device(s) that is/are configured to sense and collect personal physiological (and optionally, other types of) data generated by, associated with, or of the user 110, such as those previously discussed, e.g., heart rate monitor, CPAP machine, medical scanner, fitness monitoring clothing, etc.

External wellness or health systems 202e may include, for example, the remote fitness tracking systems 152 associated with the wellness telematics devices 202d, e.g., that store and/or analyze data collected by the wellness telematics devices 202d. In some embodiments, external wellness or health systems 202e may include one or more third-party wellness telematics systems (not shown) which may provide, for example, telemetry data (e.g., fine-grained sensor information), summarized wellness data (e.g., coarse-grained aggregated information), and/or other types of sensed physiological and/or wellness data generated by the user 110. Additionally or alternatively, external wellness or health systems 202e may provide other types of wellness-related data 148 associated with the user 110, such as indications of general medical conditions (e.g., chronic diseases, medications, etc.) and/or other medical, health, and/or wellness data of the user 110 that has been obtained and stored, for example, at a medical or health provider of the user 110.

Another data source of the data flow 202 may include one or more manual data source(s) 202f. The manual data source 202f may provide humanly reported data, e.g., by the user 110, a proxy, or a third party. The humanly reported data may include portions of the vehicle-related data 140, wellness-related data 142, context-related data 145, and/or other data 148 related to mitigating drowsy or sleepy driving. In embodiments, the manual data source(s) 202f may include data that is entered at a respective user interface of the mobile computing device 112, the on-board computing device 114, the remote computing system 135, the fitness tracking system 152, and/or the remote telematics systems 150. For example, via respective manual data sources 202f, a user 110 may self-report various vehicle-related data 140 such as odometer readings, personnel at an operations center may override and/or correct user-reported vehicle-related data, a health coach may enter the user's weight, blood pressure, and/or other wellness-related data, etc.

Yet another data source of the data flow 202 may include other external data systems 202g that may provide other types of data related to mitigating drowsy and/or sleepy driving. For example, external system 202g may provide historical insurance claim and/or historical telematics data of the driver, shift work and/or other job-related data, and/or any other types of data which may be related to mitigating drowsy or sleepy driving.

As illustrated in FIG. 3, devices that provide source data in the data flow 200 (e.g., vehicle telematics devices 202a and/or wellness telematics devices 202d) may additionally provide respective data 149 that is indicative of the respective health and/or operations of the data source device 202a, 202d, e.g., "device information data 149." For example, vehicle telematics devices 202a and/or wellness telematics devices 202d may provide device information data 149 such as device status, diagnostic, and/or other data that is indicative of the quality of operations and/or communications of its respective data source device 202a, 202d.

The data 140, 142, 145, 148, 149 that is generated by data sources 202 may be received at a data ingestor 205, and the data ingestor 205 may perform various checks on the received data 140, 142, 145, 148, 149. For example, the data ingestor 205 may perform one or more security checks 205a to authenticate and/or authorize data sources 202 from which the data 140, 142, 145, 148, 149 was received, and/or to perform any other suitable security check 205a to verify and/or validate the data source 202, and/or to verify and/or validate that the received data 140, 142, 145, 148, 149 has not been compromised. Additionally or alternatively, the data ingestor 205 may perform one or more regulatory checks 205b that may be required by one or more jurisdictions (e.g., federal, state, provincial, etc.) while collecting various types of telematics data 140, 142, 145, 148, 149. For example, based upon jurisdictional restrictions, restricted telematics data may be removed by the regulatory checks 205b and optionally logged, e.g., for use in troubleshooting regulatory compliance. Of course, other types of checks 205c on the received telematics data 140, 142, 145, 148, 149 may be additionally or alternatively performed by the data ingestor 205, if desired.

Data 140, 142, 145, 148, 149 may be received at a data interpreter 208, e.g., via the data ingestor 205 (as shown in FIG. 3) and/or directly from the data sources 202 (not shown in FIG. 3). Generally speaking, the data interpreter 208 may be configured to collectively interpret the received data 140, 142, 142, 145, 148, 149 to determine, detect, and/or predict a drowsy or sleepy driving condition of the user 110, and in some embodiments, a degree of drowsy or sleepy driving, a likelihood of drowsy or sleepy driving, a time estimate corresponding to an occurrence and/or a duration of the drowsy or sleepy driving condition, among other data and information that is indicative and/or predictive of drowsy or sleeping driving states. As such, the data interpreter 208 may perform one or more tasks or functions towards this purpose. For example, the data interpreter 208 may perform an initial data quality check 208a to, for example, validate values of the data 140, 142, 145, 148, 149 and/or make corrections when possible, e.g., by using default values. Additionally or alternatively, the data interpreter 208 may perform one or more data transformations 208b of the data 140, 142, 145, 148, 149, e.g., to standardized data element names and data values from various data sources 202, to smooth received data over time, to determine device orientation, to reduce device noise, and/or to perform additional data quality checks. Still additionally or alternatively, the data interpreter 208 may perform one or more data summarizations 208c of the data 140, 142, 145, 148, 149 to aggregate or abstract data by various characteristics, such as over a time period, at re-occurring times such as after work or after exercising, driving over roads with certain topologies, etc.

Furthermore, the data interpreter 208 may additionally or alternatively analyze the received data 140, 142, 145, 148, 149 and/or any generated data summarizations 208c to determine, generate, discover, and/or learn 208d information pertaining to drowsy and/or sleepy driving related to the user 110. In an embodiment, the learned information 208d may include a driving profile of the user 110. The driving profile may be generated based upon, for example, the vehicle-related data 140 and/or context-related data 145, and may be indicative and/or predictive of typical driving behaviors of the user 110 in various driving environments, contexts, and conditions. The driving profile may include a driving timeline or other time-stamped data indicative of the driving behaviors of the user 110, for instance. The learned information 208d may also include a sleep profile of the user 110, which may be indicative and/or predictive of typical sleep patterns and/or quality of the user 110. The user's sleep profile may be generated based upon, for example, the wellness-related data 142, and may include a sleep timeline or other time-stamped data indicative of amounts, durations, and/or quality of sleep of the user 110, in some embodiments.

The learned information 208d may include descriptive and/or predictive correlations or associations between various types of vehicle-related data 140 and wellness-related data 142 (and optionally, context-related data 145 and/or other data 148) associated with the user 110. In an embodiment, the driving profile of the user 110 may be compared against the sleep profile 110 of the user to determine descriptive and/or predictive correlations or associations between driving behaviors and characteristics of the sleep achieved by the user. For example, comparing the driving profile of the user 110 with the sleep profile of the user 110 may include determining a total number of hours of uninterrupted sleep achieved by the user in a predetermined period preceding a time during which the vehicle 108 was being driven by the user, determining a number of REM cycles achieved by the user in the predetermined period preceding the time during which the vehicle 108 was being driven by the user 110, etc. In some embodiments, at least some of the learned information 208d may be generated without generating a driving profile and/or a sleep profile of the user 110. In some embodiments, various time-stamped vehicle-related data 140, wellness-related data 142, context-related data 145, and/or other data 148 may be analyzed or processed (e.g., by the data interpreter 208) by using any one or more suitable statistical and quantitative analysis and/or machine learning techniques to determine descriptive and/or predictive correlations or associations between the various types of data 140, 142, 145, 148 and/or discover other types of learned information 208d. For example, but not limited to, regression analysis, cluster analysis, multivariate analysis, data modeling, random tree, random forest, Bayesian techniques, stacking, and/or other types of statistical/quantitative analyses and/or learning techniques may be utilized by the data interpreter 208 to generate at least some of the learned information 208d.

As such, the learned information 208d may be situational, temporal, contextual, etc. with respect to vehicle behaviors, conditions, and/or operations as well as wellness conditions, and, in some embodiments, with additional respect to contextual or environmental conditions or other conditions. For example, the data flow 200 may interpret received data 140, 142, 145, 148, 149 associated with a particular driver 110 to discover or determine that, typically, if a particular driver 110 had sleep quality of Q1 in the 24 hours prior to driving and the particular driver 110 ingests a meal of C calories, the particular driver 110 is likely to reach a drowsy and/or sleepy state of a particular level three hours after ingesting the meal, whereas if the particular driver 110 had a sleep quality Q2 in the 24 hours prior to driving, where Q2=½(Q1), and the particular driver 110 ingests a meal of C calories, the particular driver 110 is likely to reach a drowsy and/or sleepy state of the particular level two hours after ingesting the meal. On the other hand, for received data 140, 142, 145, 148, 149 associated with a different driver, the data flow 200 may determine that for a sleep quality Q1 and a meal of C calories, the different driver is likely to reach a drowsy and/or sleepy state of the particular level seven hours after ingesting the meal, and that for a sleep quality of Q2 and a meal of C calories, the different driver is likely to reach the drowsy and/or sleepy state of the particular level six hours after ingesting the meal. Accordingly, as the interpreted or learned information 208d is based upon sensed data (e.g., vehicle-related data 140, wellness-related data 142, context-related data 145, and/or other types of data 148) that is particular to each individual driver 110 (which may be collected and received over time), the leanings and information 208d generated by the data flow 200 with respect to drowsy and/or sleepy driving may be specific to each individual driver 110 and to various combinations of vehicle, wellness, contextual, and/or other conditions, e.g., in magnitude and/or timing.

Of course, the data interpreter 208 is not limited to performing the tasks or functions 208a, 208b, 208c, 208d illustrated in FIG. 3, but may perform additional, less, or alternate data processing tasks or functions of differing types to thereby collectively interpret the received data 140, 142, 145, 148, 149 (that is, to interpret two or more different types of data 140, 142, 145, 148, 149 and their inter-relationships, if any) to determine the presence, likelihood, and/or other information related to drowsy and/or sleepy driving of the user 110. For example, one or more other tasks or functions 208e may be utilized by the data interpreter 208 to interpret, analyze, and/or discover information across multiple types of received data 140, 142, 145, 148, 149 with respect to drowsy and/or sleepy driving in addition to or instead of any one or more of the other tasks/functions 208a, 208b, 208c, 208d.

The data interpreter 208 may provide an indication 210 of its interpretation of the received data 140, 142, 145, 148, 149 with respect to drowsy and/or sleepy driving of the user 110 to be used in mitigating the effects and/or danger of the user 110 driving while drowsy or sleepy. For example, the interpreted indication 210 may indicate a detected presence of drowsy or sleepy driving state of the user 110 or a predicted presence of a drowsy or sleepy driving state of the user (and, optionally predicted time of occurrence of such a state), and optionally a degree or level of drowsiness and/or sleepiness, and/or a respective confidence level of the interpreted indication 210.

In an embodiment, the interpreted indication 210 may be provided to the mobile computing device 112, the on-board computing device 114, and/or the personal health or fitness tracking device 120. Upon receipt of the interpreted indication 210, in an embodiment, the mobile computing device 112, the on-board computing device 114, and/or the personal tracking device 120 may present an alert and/or a warning at its respective user interface (e.g., a visual interface, and auditory interface, vibratory interface, and/or any other suitable user interface) to alert or warn the user 110 that a drowsy and/or sleepy driving state has been detected or predicted. If desired, the alert and/or warning may be accompanied by suggestions for mitigating the detected or predicted drowsy and/or sleepy driving state. For example, directions to the nearest exit or rest stop may be automatically provided in conjunction with the alert and/or warning. As such, the driver 110 may be informed of the detected or predicted drowsy and/or sleepy state of which the driver 110 may not have been previously aware, where the detection or prediction is based on sensed data (e.g., currently sensed data and/or sensed data over time) and not a mere perception of the driver 110. It is noted that the interpreted indication 210 may be provided to the mobile computing device 112 and/or the personal tracking device 120 even if such devices 112, 120 are not currently on-board the vehicle 108. Similarly, the interpreted indication 210 may be provided to the mobile computing device 112, the personal tracking device 120, and/or the on-board computing device 114 irrespective of whether or not the vehicle 108 is operating or otherwise turned on.

In some situations, upon receipt of the interpreted indication 210 at the mobile computing device 112 and/or at the on-board computing device 114 of the vehicle 108, the mobile computing device 112 and/or the on-board computing device 114 may automatically take action and send commands to automatically change the behavior of at least one device or system that controls at least some operations of the vehicle 108 and/or parts of the vehicle 108 to mitigate the effects of drowsy and/or sleepy driving. For example, if the interpreted indication 210 indicates that the driver 110 is presently in a drowsy and/or sleepy state above a particular threshold, the device(s) 112, 114 may send a command to disable the ignition of the vehicle 108 so that the driver 110 is not able to start the vehicle 108. In another example, if the interpreted indication 210 indicates that the driver 110 is presently in a drowsy and/or sleepy state between two thresholds, the device(s) may send a command to automatically turn on the emergency flashers or hazard lights of the vehicle 108. Other actions which may be automatically performed upon receipt of the interpreted indication 110 at the vehicle 108 are envisioned to thereby mitigate the effects of drowsy and/or sleepy driving and increase the safety of the driver 110 of the vehicle 108 and/or increase the safety of the driver 110, and/or other drivers and pedestrians in the vicinity of the vehicle 108.

Further, in some embodiments, the interpreted indication 210 may be provided to the remote computing system 135 and/or to the fitness tracking system 152, e.g., to provide redundancy of communications when the mobile device 112, on-board computing device 114, and/or personal tracking device 120 are not accessible; for long-term data storage in the data storage devices 138, for further analysis and information discovery, etc.

Still further, in some embodiments, the interpreted indication may be provided to one or more other computing systems (e.g., as represented in FIG. 1 by reference 155) for use in mitigating the effects of drowsy and/or sleepy driving. In an example scenario, the one or more other computing systems 155 may include one or more other vehicles to which the vehicle 108 is communicatively connected (e.g., via one or more wireless networks 130). For example, upon receipt of an interpreted indication 210 indicative of a detected drowsy state of the driver 110 of the vehicle 108, the computing device(s) 112, 114 on-board the vehicle 108 may notify other communicatively-connected vehicles in the vicinity of the vehicle 108 of potential abnormal operations of the vehicle 108 so that the drivers of the other vehicles may take more caution when in the vicinity of the vehicle 108. In another example scenario, the one or more other computing systems 155 may be communicatively connected to the remote computing system 135 and may host various applications thereon related to the mitigation of drowsy and/or sleepy driving. Upon receipt of the interpreted indication 210, the remote computing system 135 may provide (e.g., via the network 130) information related to the interpreted indication 210 to one or more other application-hosting computing systems for ingestion and processing by the various applications operating to mitigate the effects or dangers of drowsy and/or sleepy driving. For example, the interpreted indication 210 may be utilized by the one or more other application-hosting computing systems (along with other data corresponding to factors other than drowsy and/or sleepy driving) to rate the driving performance of the driver 110; to determine a risk profile of driver 110; to determine, update, and/or adjust insurance terms of an insurance policy corresponding to the driver 110 and/or to the vehicle 108; to educate the driver 110 with regard to what factors (e.g., types of factors, their respective magnitudes, frequencies of occurrence, durations, etc. and/or various combinations of factors) increase and/or decrease the driver's risk of drowsy and/or sleepy driving; to provide incentives (e.g., insurance discounts and/or other incentives) for the driver 110 to avoid and/or decrease occurrences of drowsy and/or sleepy driving, and/or other types of drowsy and/or sleepy driving mitigation applications. It is noted that while FIG. 1 illustrates the other computing system(s) 155 as being separate and distinct from the remote computing system 135, in some embodiments, at least one of the one or more other computing systems 155 may be integral with the remote computing system 135.

FIG. 4 includes a flow diagram of an example method 230 for mitigating drowsy and/or sleepy driving. The method 230 may operate in conjunction with the system 100 of FIG. 1, the personal health or fitness tracking device 120 of FIG. 2, the data flow diagram 200 of FIG. 3, and/or with other systems, devices, and data flows. However, for ease of discussion, the method 230 is discussed herein with simultaneous reference to FIGS. 1-3. Further, the method 230 may include additional, less, or alternate actions, in certain embodiments.

The method 230 may include collecting 232 vehicle-related telematics data, such as vehicle-telematics data 140, at least a portion of which may be generated by a set of sensors positioned and configured to monitor at least one of a condition or a behavior of a vehicle operated by driver. The set of sensors may include, for example, and as discussed above, the on-board vehicle sensors 118, sensors that are included in the mobile computing device 112, sensors that are included in the on-board computing device 114, and/or other sensors that are on-board the vehicle 108. Additionally or alternatively, the sensors monitoring the behaviors, conditions, and environments of the vehicle may include sensors that are disposed external to and separately from the vehicle 108, but nonetheless are positioned and configured to monitor the environment in which the vehicle 108 is operating (e.g., infrastructure sensors, weather sensors, traffic sensors, security sensors, etc.).

The method 230 may further include collecting 235 wellness-related telematics data, such as wellness-related telematics data 142, at least a portion of which may be generated by one or more health or fitness personal tracking devices that are configured and may be positioned to sense various physiological conditions of the driver (while the driver is operating the vehicle 108 and while the driver is not operating the vehicle, for example). For example, the personal tracking device may be the personal health or fitness tracking device 120. The personal tracking device may generate wellness-related telematics data based on the sensed physiological conditions of the driver, which may be indicative of a quality and/or duration of sleep achieved by the driver, e.g., over one or more periods of time. For example, as previously discussed, sleep data may be indicative of occurrences and durations of uninterrupted sleep, occurrences and durations of disturbed sleep, a number and/or respective durations of REM cycles, a single sleep cycle, multiple sleep cycles, etc. Sleep data (as well as, in some embodiments, other wellness-telematics data that is generated by the personal tracking device) may be collected directly from the personal tracking device, e.g. via a direct wireless link. Additionally or alternatively, at least some of the sleep data may be collected from a back-end health or fitness tracking system (e.g., the remote health or fitness tracking system 152 to which the personal tracking device 120 synchronizes.

The method 230 may further include interpreting 238 the vehicle-related telematics data in conjunction with the wellness-related telematics data, thereby generating or discovering information that is indicative and/or predictive of a drowsy and/or sleepy state of the driver. Interpreting the vehicle-related telematics data in conjunction with the wellness-related telematics data may include, for example, detecting a presence of a drowsy and/or sleepy state of the driver, and optionally, a degree of drowsiness and/or sleepiness. Interpreting the vehicle-related telematics data in conjunction with the wellness-related telematics data may additionally or alternatively include predicting an occurrence of a presence of the drowsy and/or sleepy state of driver, and optionally a degree of drowsiness and/or sleepiness and/or a predicted time at which the drowsy and/or sleepy state of the driver is likely to occur. As such, interpreting 238 the vehicle-related telematics data in conjunction with the wellness-related telematics data may include utilizing one or more statistical analysis techniques and/or one or more machine learning techniques to discover the information indicative of the drowsy and/or sleepy state of the driver.

In some embodiments (not shown in FIG. 4), the method 230 may further include collecting context-related telematics data, such as the context-related telematics data 145, and utilizing the contextual-related telematics data in conjunction with the vehicle-related telematics data and the wellness-related telematics data to generate information indicative and/or predictive of the drowsy and/or sleepy state of the driver. Context-related telematics data may be collected from one or more third-party sources, such as other vehicles, infrastructure sensing systems, weather feeds, and/or any other sources that provide telematics data indicative of the environment in which the vehicle is operating, for example. In a similar manner, other types of data 148 may be collected and utilized to generate information indicative and/or predictive of a drowsy and/or sleepy state of the driver.

The method 230 may include transmitting 240 one or more commands for one or more mitigating actions to be performed, where the one or more commands, the one or more mitigating actions, and/or the respective recipients of the command(s) may be determined based upon the generated information indicative of the drowsy and/or sleepy state of the driver. Generally speaking, the one or more mitigating actions may prevent or lessen undesirable effects of the driver operating the vehicle while in a drowsy and/or sleepy state. For example, the one or more mitigating actions may lessen the chance of (or in some cases, prevent) an accident from happening due to the driver's drowsy and/or sleepy state, thereby increasing driving safety to the driver and to other people and vehicles in the driver's vicinity.

Transmitting the one or more commands for one or more mitigating actions to be performed (block 240) may include, for example, transmitting one or more commands to one or more components of the vehicle to instruct the component(s) to automatically change one or more operating behaviors of the vehicle (e.g., disable the ignition, decrease vehicle speed, turn on flashers, etc.). Additionally or alternatively, transmitting the one or more commands for the one or more mitigating actions to be performed (block 240) may include transmitting a command to display, at a user interface onboard the vehicle, a notification of the generated information relating to the drowsy and/or sleepy state of the driver. The notification may include an alert and/or a warning of the detected and/or predicted drowsy and/or sleepy state of the driver, and optionally may also include suggested mitigating actions for the driver to take. The notification may be a visual, auditory, and/or physical notification, as desired.

In some embodiments, transmitting 240 the one or more commands for one or more mitigating actions to be performed may include transmitting an indication of the generated information indicative of the drowsy and/or sleepy state of the driver for inclusion in determining a risk profile of the driver. For example, discovered information that is indicative of how often, when, and/or where the driver operates the vehicle while drowsy and/or sleepy may be combined with other detected driving data related to the driver (such as traffic violations, excessive speed, extreme cornering, etc.) to determine the driver's risk profile. The driver's risk profile may then be utilized for various purposes, such as for determining terms of an insurance policy, e.g., the insurance policy's structure, features, and/or costs. In some embodiments, generated information indicative of the drowsy and/or sleepy state of the driver may be utilized in generating an incentive for the driver to decrease the number of occurrences of driving while drowsy and/or sleepy. For example, the driver may be incentivized by an insurance discount or other monetary compensation to decrease the number of instances (e.g., over time) that the driver operates the vehicle while drowsy and/or sleepy. Subsequently, if the generated information indicative of the drowsy and/or sleepy states of the driver demonstrates that the driver has been in compliance with the incentive, the incentive may be granted to the driver.

FIG. 5 illustrates a block diagram of an exemplary computing device 300 in accordance with an exemplary aspect of the present disclosure. Computing device 300 may be implemented as a special-purpose computing device that is particularly configured to mitigate drowsy and/or sleepy driving. For example, the computing device 300 may be configured with one or more tangible, non-transitory, computer-readable storage media or memories storing particular computer-executable instructions to perform at least a portion of embodiments of the method 230 of FIG. 4. Additionally or alternatively, the mobile computing device 112, the on-board computing device 114, the remote computing system 135, and/or the one or more application-hosting computing systems 155 may each include respective, one or more particularly-configured instances of the computing device 300 to thereby mitigate drowsy and/or sleepy driving. At any rate, the computing device 300 may be utilized in conjunction with any of the systems, methods, devices, apparatuses, and/or techniques for mitigating drowsy or sleepy driving and improving driving safety based on vehicle-related and sleep-related telematics data described herein.

As illustrated in FIG. 5, computing device 300 may include a display 302, a graphics processing unit (GPU) 305, a location acquisition unit 308, a speaker/microphone 310, a sensor array 312, a user interface 315, a communication unit 318, and/or a controller 320.

In one aspect, the controller 320 may include a program memory 322, a microprocessor (MP) 325, a random-access memory (RAM) 328, and/or an input/output (I/O) interface 330, each of which may be interconnected via an address/data bus 332. The controller 320 may be implemented as any suitable type and/or number of processors, such as a host processor for the relevant device in which the computing device 300 is implemented, for example. In some aspects, the controller 320 may be configured to communicate with additional data storage mechanisms or devices that are not shown in FIG. 5 for purposes of brevity (e.g., one or more hard disk drives, optical storage drives, solid state storage devices, etc.) that reside within or are otherwise associated with and/or accessible to the computing device 300.

Program memory 322 may store data used in conjunction with one or more functions performed by computing device 300 to facilitate the interaction between computing device 300 and one or more other devices. For example, if computing device 300 is implemented as a mobile computing device (e.g., mobile computing device 112, as shown in FIG. 1), then program memory 322 may store one or more programs, applications, algorithms, etc. that, when executed by controller 320, facilitate the interaction between mobile computing device 112 and (i) one or more networks (e.g., network 130), (ii) external computing devices or systems (e.g., external computing devices and/or systems 135, 150, 152, 155), (iii) vehicle on-board computers (e.g., on-board computing device 114), (iv) personal health or fitness tracking devices (e.g., personal tracking device 120), etc.

In various aspects, program memory 322 may be implemented as a non-transitory, tangible computer readable media configured to store computer-readable instructions, that when executed by controller 320, cause controller 320 to perform various acts. Program memory 322 may include an operating system 342, one or more software applications 344, and one or more software routines 352. To provide another example, program memory 322 may include other portions to store data that may be read from and written to by the processor 325, such as data storage 360, for example.

In one aspect, one or more MPs (micro-processors) 325 may be configured to execute one or more of software applications 344, software routines 352 residing in program memory 322, and/or other suitable software applications. Operating system 342 may be implemented as any suitable operating system platform depending upon the particular implementation of computing device 300. For example, if computing device 300 is implemented as a mobile computing device, operating system 342 may be implemented as a mobile OS platform such as the iOS®, Android™, Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. Additionally, in one embodiment, data storage 360 may store data such as application data for the one or more software applications 344, routine data for the one or more software routines 352, geographic location data and/or telematics data, etc.

Display 302 may be implemented as any suitable type of display and may facilitate user interaction with computing device 300 in conjunction with user interface 315. For example, display 302 may be implemented as a capacitive touch screen display, a resistive touch screen display, etc. In various embodiments, display 302 may be configured to work in conjunction with controller 320 and/or GPU 305 to display alarms, warnings, notifications, and other information related to mitigating drowsy and/or sleepy driving.

Communication unit 318 may be configured to support separate or concurrent communications, which may be the same type of communication protocol or different types of communication protocols. For example, communication unit 318 may be configured to facilitate communications between computing device 300 and one or more external computing devices (e.g., external computing devices and/or systems 135, 150, 152, 155) via cellular or other types of longer-range wireless communications in addition to facilitating shorter-range communications (e.g., BLUETOOTH communications) between computing device 300 and any other computing device that is on-board the vehicle 108 (e.g., computing devices 112, 114). Generally speaking, the communication unit 318 may communicate with the other computing systems and devices (e.g., devices or systems 112, 114, 135, 150, 152, 155) via the network 130 or directly via any suitable wireless communication protocol network, such as wireless telephony (e.g., GSM, CDMA, LTE, etc.), Wi-Fi (802.11 standards), WiMAX, Bluetooth, infrared or radio frequency communication, etc. Further, the communication unit 318 may receive data from other devices, provide input signals to the controller 320 via the I/O circuit 330, and/or transmit data generated by the controller 320.

Communication unit 318 may be configured to transmit data and/or to receive data in accordance with any suitable communications schedule, on demand, upon reception or detection, etc. For example, communication unit 318 may be configured to transmit at least some of data 140, 142, 145, 148, 149 every 15 seconds, every 30 seconds, every minute, etc. The data 140, 142, 145, 148, 149 may be sampled in accordance with any suitable sampling period, on demand, upon reception or detection, etc. When being transmitted by the communications unit 318 according to a schedule, the data 140, 142, 145, 148, 149 may include a log or collection of data 140, 142, 145, 148, 149 that was sampled since the last data transmission. A suitable communication schedule may be selected as a tradeoff between a desired update interval, speed of information delivery, battery usage of computing device 300, and/or other considerations, when applicable.

Additionally or alternatively, aspects include communication unit 318 being configured to conditionally send data, which may be particularly advantageous when computing device 300 is implemented as a mobile computing device 112, as such conditions may help reduce power usage and prolong battery life. For example, communication unit 318 may be configured to only transmit data 140, 142, 145, 148, 149 that has been sampled since the last transmission. Controller 320 may determine whether has been sampled since the last transmission by, for example, analyzing a memory address range (e.g., in data storage 360, RAM 328, etc.) associated with the storage of the telematics data and comparing the contents of this buffer to a known range of valid values.

To provide another example, aspects include communication unit 318 being additionally or alternatively configured to only transmit telematics data 140, 142, 145, 148, 149 when computing device 300 is connected to a power source (e.g., an in-vehicle charger or another type of power supply). To provide still another example, aspects include communication unit 318 being additionally or alternatively configured to only transmit telematics data 140, 142, 145, 148, 149 when communication unit 318 is connected to and/or communicating with a device associated with the vehicle 108. This may include, for example, identifying a BLUETOOTH connection as being provided by a valid vehicle 108 to satisfy this condition upon installation and/or setup of the relevant application or program executed by computing device 300 to facilitate the functionality described herein.

Location acquisition unit 308 may be configured to generate geographic location data utilizing any suitable global positioning techniques. For example, location acquisition unit 308 may communicate with one or more satellites and/or wireless transmitters to determine a location of computing device 300. Location acquisition unit 308 may use "Assisted Global Positioning System" (A-GPS), satellite GPS, or any other suitable global positioning protocol (e.g., the GLONASS system operated by the Russian government, the Galileo system operated by the European Union, etc.) to determine a geographic location of computing device 300.

In one aspect, location acquisition unit 308 may periodically store one or more geographic locations of computing device 300 as geographic location data in any suitable portion of memory utilized by computing device 300 (e.g., program memory 322, RAM 328, etc.) and/or to another device (e.g., another mobile computing device, an external computing device, etc.). In this way, location acquisition unit 308 may sample the location of computing device 300 in accordance with any suitable sampling rate (e.g., every 5 seconds, 10 seconds, 30 seconds, etc.) and store this geographic location data representing the position of computing device 300, and thus the vehicle 108 in which it is travelling, over time.

Speaker/microphone 310 may be configured as one or more separate devices. Speaker/microphone 310 may include a microphone configured to detect sounds and to convert sounds to data suitable for communications via communications unit 318. Speaker/microphone 310 may additionally or alternatively include a speaker configured to play sound in response to data received from one or more components of computing device 300 (e.g., controller 320). In one embodiment, speaker/microphone 310 may be configured to play audible alerts, warnings, and/or other information related to mitigating drowsy and/or sleepy driving.

User-interface 315 may be implemented as any suitable device configured to collect user input, such as a "soft" or touchscreen keyboard displayed on display 302 of computing device 300, a keyboard attached to computing device 300, an external keyboard communicating via a wired or a wireless connection (e.g., a BLUETOOTH keyboard), an external mouse, etc.

Sensor array 312 may be configured to measure any suitable number and/or type of sensor metrics as part of the data 140, 142, 145, 148, 149. In one aspect, sensor array 312 may include one or more on-board sensors 118 positioned to determine the speed, force, heading, and/or direction associated with movements of computing device 300 and, thus, a vehicle 108 in which computing device 300 is positioned. To generate one or more sensor metrics (e.g., sensed data), sensor array 312 may include, for example, one or more cameras, accelerometers, gyroscopes, magnetometers, barometers, thermometers, compasses, magnetometers, proximity sensors, light sensors, Hall Effect sensors, audio or video recorders, etc.

In one aspect, sensor array 312 may include one or more cameras and/or image capture devices. When sensor array 312 is implemented with one or more cameras, these cameras may be configured as any suitable type of camera configured to capture and/or store images and/or video. For example, when computing device 300 is mounted in the vehicle 108, the camera may be configured to store images and/or video data of the road in front of the vehicle in which it is mounted, and to store this data to any suitable portion of program memory 322 (e.g., data storage 360). Controller 320 and/or MP 325 may analyze this data to generate sensed data 145 descriptive of the context and/or environment in which the vehicle 108 is operating, for example.

The MP 325 may additionally or alternatively communicate with other portions of computing device 300 to obtain one or more sensor metrics (e.g., sensed data 140, 142, 145, 148, 149) even though these sensor metrics may not be measured by one or more sensors that are part of sensor array 312. For example, MP 325 may communicate with one or more of location acquisition unit 308, communication unit 318, and/or controller 320 to obtain data such as timestamps synchronized to the sampling of one or more sensor metrics (which may be measured to within hundredths of a second or smaller resolutions), geographic location data (and correlated timestamps thereof), a velocity based upon changes in the geographic location data over time, a battery level of computing device 300, whether a battery of computing device 300 is charging, whether computing device 300 is being handled or otherwise in use, an operating status of computing device 300 (e.g., whether computing device 300 is unlocked and thus in use).

In one aspect, sensor array 312 may sample one or more sensor metrics based upon one or more conditions being satisfied. For example, sensor array 312 may determine, based upon gyroscope sensor metrics, communication with controller 320, etc., whether computing device 300 is in use. If computing device 300 is in use (e.g., when implemented as a mobile computing device) then the movement of computing device 300 within the vehicle may not truly represent the vehicle motion, thereby causing sensor metrics sampled during this time to be erroneous. Therefore, aspects include sensor array 312 sampling the one or more sensor metrics when computing device 300 is not in use, and otherwise not sampling the one or more sensor metrics.

Additionally or alternatively, the controller 320 may be configured to obtained external data or metrics (e.g., telematics data 140, 142, 145, 148, 149) from other sources that are communicatively connected to the computing device 300, e.g., via the communications interface 318. In some aspects, software applications 344 and/or software routines 352 may reside in program memory 322 as default applications that may be bundled together with the OS of computing device 300. For example, web browser 348 may be part of software applications 344 that are included with OS 342 implemented by computing device 300.

In other aspects, software applications 344 and/or software routines 352 (such as software applications 346, 354, 356, and 358) may be installed on computing device 300 as one or more downloads, such as an executable package installation file downloaded from a suitable application store via a connection to the Internet. For example, software applications 346, 354, 356, and 358 may be stored to suitable portions of program memory 322 upon installation of a package file downloaded in such a manner. Examples of package download files may include downloads via the iTunes store, the Google Play Store, the Windows Phone Store, downloading a package installation file from another computing device, etc. Software applications 344, software routines 352, and/or software applications 346, 354, 356, and 358 may carry out embodiments of at least portions of the methods described herein, in an embodiment. For example, the MP 325 may be adapted and configured to execute any one or more of the applications 344, routines 352, and/or applications 346, 354, 356, and 358 residing in the program memory 322 to perform at least portions of the embodiments of the methods described herein to mitigate drowsy and/or sleepy driving.

Further, although FIG. 5 depicts controller 320 as including one program memory 322, one MP 325, and one RAM 328, controller 320 may include any suitable number of program memories 322, MPs 325, and RAMs 328. Furthermore, although FIG. 5 depicts controller 320 as having a single I/O interface 330, controller 320 may include any suitable number and/or types of I/O interfaces 330. In various aspects, controller 320 may implement RAM(s) 328 and program memories 322 as any suitable type of tangible memory, such as non-transitory computer readable memories, semiconductor memories, magnetically readable memories, and/or optically readable memories, for example.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. Additionally, certain embodiments are described herein as including logic or a number of routines, subroutines, applications, or instructions. These may constitute either software (e.g., code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software or by software modules (e.g., an application or application portion) as a hardware module that operates to perform certain operations as described herein.

In various embodiments, a hardware module may be implemented mechanically and/or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which modules are temporarily configured (e.g., programmed), each of the modules need not be configured or instantiated at any one instance in time. For example, where the modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware and/or software modules may provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, one module may perform an operation and store the output of that operation in a memory device to which it is communicatively coupled. A further module may then, at a later time, access the memory device to retrieve and process the stored output. Hardware and/or software modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules. Moreover, the systems and methods described herein are directed to an improvement to computer functionality and improve the functioning of conventional computers.

Similarly, the methods or routines described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations (e.g., cloud computing systems, networked servers, etc.).

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Further, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

This detailed description is to be construed as exemplary only and does not describe every possible embodiment, as describing every possible embodiment would be impractical, if not impossible. One may be implement numerous alternate embodiments, using either current technology or technology developed after the filing date of this application. Upon reading this disclosure, those of skill in the art will appreciate still additional alternative structural and functional designs for systems and methods for mitigating drowsy or sleepy driving through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein. It is therefore intended that the foregoing detailed description be regarded as illustrative rather than limiting, and that it be understood that it is the following claims, including all equivalents, that are intended to define the spirit and scope of this invention.

What is claimed:

1. A system for mitigating drowsy driving, the system comprising:
    a set of sensors disposed on-board a vehicle operated by a driver;
    a personal tracking device that senses one or more physiological conditions of the driver; and
    one or more computing devices communicatively connected to the set of on-board sensors of the vehicle and to the personal tracking device, the one or more computing devices including one or more processors, one or more memories, and a set of computer-executable instructions stored on the one or more memories and executable by the one or more processors to:
        collect, via one or more communication channels, vehicle-related telematics data generated by the set of on-board sensors of the vehicle;
        collect, via the one or more communication channels, wellness-related telematics data generated by the personal tracking device based on the sensed physiological conditions of the driver, the wellness-related telematics data including sleep data indicative of at least one of a quality or a duration of sleep achieved by the driver;
        collect, via the one or more communication channels, context-related telematics data indicative of an environment in which the vehicle is operating, wherein the context-related telematics data is collected from an infrastructure sensing system external to the vehicle;
        interpret the vehicle-related telematics data in conjunction with the wellness-related telematics data and the context-related telematics data, thereby generating information indicative of a drowsy state of the driver; and
        cause a mitigating action to be performed based on the generated information indicative of the drowsy state of the driver.

2. The system of claim 1, wherein the set of on-board sensors includes at least one of: a camera, another type of optical sensor, a weight sensor, a speed sensor, a noise sensor, a heat sensor, an accelerometer, another type of force sensor, a location tracking sensor, a proximity sensor, a seat belt sensor, a geo-positioning sensor, a sensor to detect an operation of an instrument included in the vehicle, a sensor to detect an operation of a system that controls one or more operational behaviors of the vehicle, or another sensor.

3. The system of claim 1, wherein the generated information indicative of the drowsy state of the driver is indicative of a detected drowsy state of the driver.

4. The system of claim 1, wherein the generated information indicative of the drowsy state of the driver is indicative of a predicted drowsy state of the driver.

5. The system of claim 1, wherein the generated information indicative of the drowsy state of the driver includes at least one of an indication of a degree of drowsiness or a predicted time of occurrence of the drowsy state of the driver.

6. The system of claim 1, wherein interpretation of the vehicle-related telematics data in conjunction with the wellness-related telematics data and the context-related telematics data includes a discovery of at least one interrelationship between at least some of the vehicle-related telematics data and at least some of the wellness-related telematics data.

7. The system of claim 6, wherein the at least one interrelationship between the at least some of the vehicle-related telematics data and the at least some of the wellness-related telematics data includes a temporal interrelationship.

8. The system of claim 1, wherein the wellness-related telematics data further includes other data indicative of other physiological conditions of the driver, and wherein the generated information indicative of the drowsy state of the driver is based on the vehicle-related telematics data, the sleep data, and the data indicative of other physiological conditions of the driver.

9. The system of claim 1, wherein causing the mitigating action to be performed comprises automatically sending, by the one or more computing devices to a component of the vehicle, a command to automatically change an operating behavior of the vehicle.

10. The system of claim 1, wherein causing the mitigating action to be performed comprises automatically sending, to a user interface on-board the vehicle, a notification of the generated information indicative of the drowsy state of the driver.

11. The system of claim 1, wherein the mitigating action comprises a utilization of the generated information indicative of the drowsy state of the driver in determining a risk profile of the driver.

12. The system of claim 1, where the mitigating action comprises a utilization of the generated information indicative of the drowsy state of the driver in determining and providing an incentive for the driver to decrease occurrences of driving while drowsy, the incentive including a discount on an insurance policy corresponding to the driver.

13. A method for mitigating drowsy driving, the method comprising:
    collecting, via one or more communication channels by one or more computing devices, vehicle-related telematics data generated by a set of sensors monitoring at least one of a condition or a behavior of a vehicle operated by a driver;
    collecting, via the one or more communication channels by the one or more computing devices, wellness-related telematics data generated by a personal tracking device that senses physiological conditions of the driver, the wellness-related telematics data based on the sensed physiological conditions of the driver, and the wellness-related telematics data including sleep data that is indicative of at least one of a quality or a duration of sleep achieved by the driver;
    collecting, via the one or more communication channels by the one or more computing devices, context-related telematics data indicative of an environment in which the vehicle is operating, wherein the context-related telematics data is collected from an infrastructure sensing system external to the vehicle;
    interpreting, at the one or more computing devices, the vehicle-related telematics data in conjunction with the wellness-related telematics data and the context-related telematics data, thereby generating information indicative of a drowsy state of the driver; and
    transmitting, by the one or computing devices, a command for a mitigating action to be performed, the command for the mitigation action based on the generated information indicative of the drowsy state of the driver.

14. The method of claim 13, wherein at least one of:

(i) collecting the vehicle-related telematics data generated by the set of sensors comprises collecting the vehicle-related telematics data generated by at least one of: a camera, another type of optical sensor, a speed sensor, a weight sensor, a noise sensor, a heat sensor, an accelerometer, another type of force sensor, a location tracking sensor, a proximity sensor, a seat belt sensor, a geo-positioning sensor, a sensor to detect an operation of an instrument included in the vehicle, a sensor to detect an operation of a system that controls one or more operational behaviors of the vehicle, or another sensor; or (ii) collecting, via the one or more communication channels, the wellness-related telematics data generated by the personal tracking device comprises at least one of collecting at least a first portion of the wellness-related telematics data directly from the personal tracking device via a wireless communication channel or collecting at least a second portion of the wellness-related telematics data from a fitness tracking system to which the personal tracking device is synchronized.

15. The method of claim 13, wherein interpreting the vehicle-related telematics data in conjunction with the wellness-related telematics data and the context-related telematics data, thereby generating the information indicative of the drowsy state of the driver comprises detecting a presence of the drowsy state of the driver and a degree of drowsiness.

16. The method of claim 13, wherein interpreting the vehicle-related telematics data in conjunction with the wellness-related telematics data and the context-related telematics data, thereby generating the information indicative of the drowsy state of the driver comprises predicting an occurrence of a presence of the drowsy state of the driver at a particular time.

17. The method of claim 13, wherein interpreting the vehicle-related telematics data in conjunction with the wellness-related telematics data and the context-related telematics data comprises discovering an interrelationship between at least some of the vehicle-related telematics data and at least some of the wellness-related telematics data by using at least one of a statistical analysis technique or a machine learning technique.

18. The method of claim 13, wherein transmitting the command for the mitigating action to be performed comprises at least one of:

transmitting a command to one or more components of the vehicle to change an operating behavior of the vehicle; or transmitting a command to display, on a user interface on-board the vehicle, a notification of the generated information indicative of the drowsy state of the driver.

19. The method of claim 13, wherein transmitting the command for the mitigating action to be performed comprises transmitting an indication of the generated information indicative of the drowsy state of the driver for inclusion in determining a risk profile of the driver.

20. The method of claim 13, wherein transmitting the command for the mitigating action to be performed comprises transmitting an indication of the generated information indicative of the drowsy state of the driver for use in generating an incentive for the driver to reduce occurrences of driving while drowsy.

21. The method of claim 20, wherein generating the incentive for the driver to reduce occurrences of driving while drowsy comprises generating an indication of an insurance discount corresponding to the driver.

* * * * *